US006355243B1

(12) United States Patent
Novokhatny et al.

(10) Patent No.: US 6,355,243 B1
(45) Date of Patent: Mar. 12, 2002

(54) METHOD OF THROMBOLYSIS BY LOCAL DELIVERY OF ACTIVE PLASMIN

(75) Inventors: Valery V. Novokhatny, Raleigh, NC (US); Gary J. Jesmok, Richmond; Kyle A. Landskroner, Mill Valley, both of CA (US); Kathryn K. Taylor, Apex; Thomas P. Zimmerman, Raleigh, both of NC (US)

(73) Assignee: Bayer Corporation, Pittsburgh, PA (US)

( * ) Notice: Subject to any disclaimer, the term of this patent is extended or adjusted under 35 U.S.C. 154(b) by 0 days.

(21) Appl. No.: 09/438,331

(22) Filed: Nov. 13, 1999

(51) Int. Cl.[7] .......................... A61K 38/48; C12N 9/48; C12N 9/72; C12N 9/68
(52) U.S. Cl. .............................. 424/94.64; 424/94.63; 435/212; 435/215; 435/217
(58) Field of Search .................. 435/217, 215, 435/212; 424/94.64, 94.63

(56) References Cited

U.S. PATENT DOCUMENTS

| | | |
|---|---|---|
| 3,434,929 A | 3/1969 | Buck et al. |
| 3,950,513 A | 4/1976 | Jensen |
| 4,082,612 A | 4/1978 | Robbins et al. |
| 4,177,262 A | 12/1979 | Lormeau et al. |
| 4,361,652 A | 11/1982 | Uemura et al. |
| 4,361,653 A | 11/1982 | Watanabe et al. |
| 4,442,213 A | 4/1984 | Heber et al. |
| 4,446,316 A | 5/1984 | Chazov et al. |
| 4,462,980 A * | 7/1984 | Diedrichsen et al. |
| 4,908,204 A | 3/1990 | Robinson et al. |
| 5,288,489 A | 2/1994 | Reich et al. |
| 5,290,692 A | 3/1994 | Suzuki et al. |
| 5,304,383 A | 4/1994 | Eibl et al. |
| 5,328,996 A * | 7/1994 | Boyle |
| 5,472,692 A | 12/1995 | Liu et al. |
| 5,776,452 A | 7/1998 | Eibl et al. |
| 5,879,923 A | 3/1999 | Yago et al. |
| 6,139,819 A | 10/2000 | Unger et al. |

OTHER PUBLICATIONS

Ambrus, C., et al., "Insolubilized Activators of the Fibrinolysin System," *J. Med.* vol. 3, pp. 270–281 (1972).

Amris, C.J., et al., "Effect of Plasmin Therapy on Blood Coagulation and on Plasma Proteins in Patients with Cancer," *Danish Medical Bulletin*, vol. 11, No. 5; pp. 141–145 (1964).

Amris, C.J., et al., "Turnover and Distribution of [131]I–Labelled Procine Plasmin in Man and Dog," *Danish Medical Bulletin*, vol. 11, No. 5; pp. 146–152 (1964).

Anlyan, W., et al., "Experiences with Fibrinolysin in Peripheral Vascular Occlusive Disease," *The American Journal of Cardiology*, pp. 507–512 (1960).

Boucek, R., et al., "Segmental Perfusion of the Coronary Arteries with Fibrinolysin in Man Following a Myocardial Infarction," *Am. J. Cardiol.* vol. 6; pp. 525–533 (1960).

Freitag, H., et al., "Lys–plasminogen as an Adjunct to Local Intra–arterial Fibrinolysis of Carotid Territory Stroke: Laboratory and Clinical Findings," *Neuroradiology*, vol. 38; pp. 181–185 (1996).

Hedner, U., et al., "Effects of Porcine Plasmin on the Coagulation and Fibrinolytic Systems in Humans," *Blood*, vol. 51, No. 1; pp. 157–164 (1978).

Kitamoto, Y., et al., "A Femoral Vein Catheter with Immobilized Urokinase (UKFC) as an Antithrombotic Blood Access," *Trans Am Soc Artif Intern Organs*, vol. 33, pp. 136–139 (1987).

Larsen, V., "Fibrinolytic Enzyme in the Treatment of Patients with Cancer," *Danish Medical Bulletin*, vol. 2; No. 5; pp. 137–140 (1964).

Larson, V., et al., "Fibrinolytic Treatment with Activator–Free Porcine Plasmin," *Scand. J. Clin. Invest.* 18 (Suppl. 89); pp. 34–73 (1966).

Moser, K., "Effects of Intravenous Administration of Fibrinolysin (Plasmin) in Man," *Circulation*, vol. 20; pp. 42–55 (1959).

Sherry, S., "The Origin of Thrombolytic Therapy," *J. Am. Coll. Cardiol.*, vol. 14, No. 4; pp. 1085–1092 (1989).

Verstraete, M., "The Fibrinolytic System: from Petri Dishes to Genetic Engineering," *Thrombosis and Haemostasis*, vol. 74(1), pp. 25–35 (1995).

Novokhatny et al. Blood, J of the Am Soc of Hematology, 92(10), Suppl. 2, Abstract 3400. Thrombolytic potential of locally delivered active plasmin (Pm): In vitro assessment and in vivo comparison with tPA in the rabbit jugular vein trombosis model, Nov. 15, 1998.*

Mizutani et al. Japanese Heart Journal, 30(5), pp. 723–732. Potential thrombolysis under selective infusion of autolotous plasmin (AP) solution, Sep. 1989.*

Kitamoto et al. Trans. Am. Soc. Artif. Organs, 33(3), pp. 136–139.A femoral vein catheter with immobilized urokinase (UKFC) as an antithrombotic blood access.*

"Activation of plasminogen by pro–urokinase"; Lijnen, H.R., Zamarron, C., Blaber, M., Winkler, M.E., Collen, D.; J. Biol. Chem. 261(1), 1253–1258, Jan. 5, 1986.

"Thrombolysis with human extrinsic (tissue–type) plasminogen activator in rabbits with experimental jugular vein thrombosis. Effect of molecular form and dose of activator, age of the thrombus, and route of administration"; Collen, D., Stassen, J.M., Verstraete, M.; J. of Clin. Invest. 71(2):368–376, Feb. 1983.

(List continued on next page.)

Primary Examiner—Christopher R. Tate
Assistant Examiner—Michele C. Flood
(74) Attorney, Agent, or Firm—Womble Carlyle Sandridge & Rice, PLLC

(57) ABSTRACT

The invention provides an improved method of thrombolytic therapy by the direct admiistration of active plasmin to a clot site via catheter. An active, stable preparation of plasmin is provided, as is a process for activation and isolation of active plasmin.

5 Claims, 12 Drawing Sheets

OTHER PUBLICATIONS

"On the structure of the stable complex between plasmin and alpha–2–antiplasmin"; Nilsson, T. and Wiman, B., FEBS Lett. 142(1):111–114, Jun. 1982.

"Human Plasminogen"; Castellino, F.J. and Powell, J.R., Meth. Enzymology 80:365–378, 1981.

"Affinity–chromatographic purification of human alpha 2–antiplasmin"; Wiman, B., Biochem. J. 191 (1):229–232, Jun. 5, 1980.

The Electrophoretically 'Slow' and 'Fast' Forms of the α2–Macroglobulin Molecule; Barrett, A.J., Brown, M.A., Sayers, C.A., Biochem. J. 181, 401–418, 1979.

"Plasminogen and Plasmin"; Robbins, K.C. and Summaria, L., Meth Enzymology 45:257–273, 1976.

"Plasminogen: purification from human plasma by affinity chromatography"; Deutsch, D.G. and Mertz, E.T.; Science 170, 1095–1096, Dec. 4, 1970.

"Controlled study of the treatment of coronary occulsion with urokinase–activated human plasmin"; Lippschutz, E.L., Ambrus, J.L., Ambrus, C.M., Constant, J., Rekate, A.C., Collins, G.L., Sokal, J.E., Am. J. Cardiology 16:93–98, Jul. 1965.

"Clinical Pharmacology of various types of fibrinolytic enzyme preparations"; Ambrus, J.L., Ambrus, C.M., Sokal, J.E., Markus, G., Back, N., Stutzman, L., Razis, D., Ross, C.A., Smith, B.H., Rekate, A.C., Collins, G.L., Kline, D.L., Fishman, J.B., Am. J. Cardiology 6:462–475, Aug. 1960.

"Comparative effectiveness of intravenous and intra–arterial fibrinolysin therapy"; Boyles, P.W., Meyer, W.H., Graff, J., Ashley, C., Ripic, R.G., Am. J. Cardiology 6:439–446, Aug., 1960.

* cited by examiner

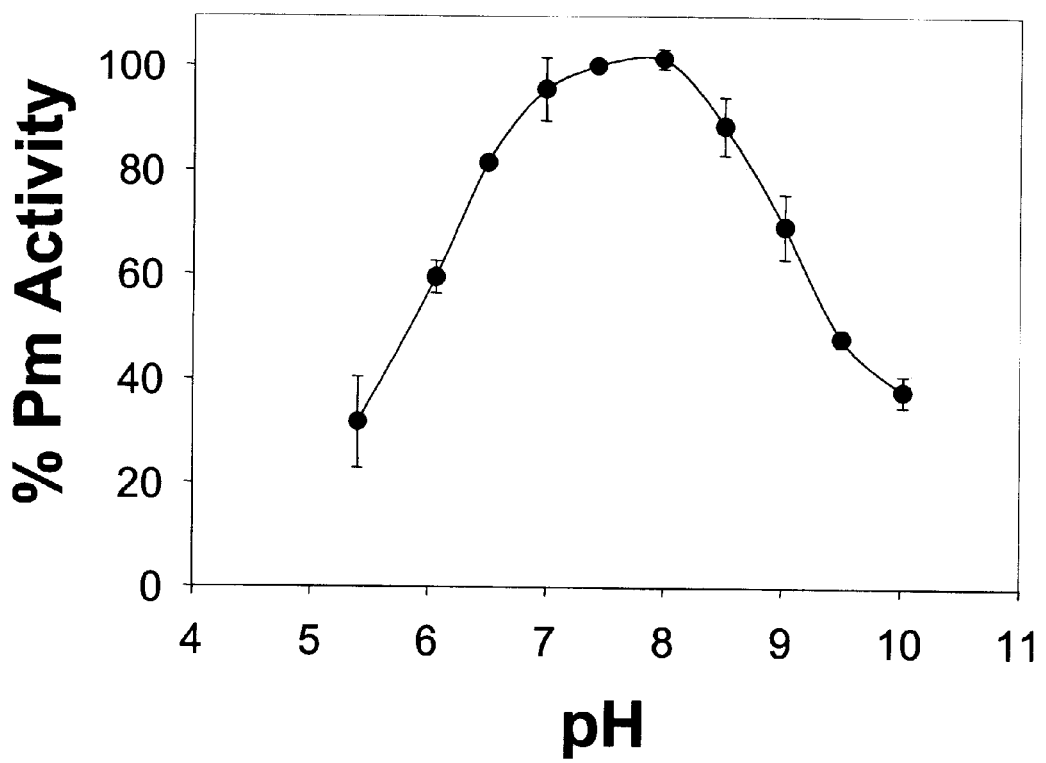
Figure 1. pH dependence of plasmin activity as measured with chromogenic substrate S2251

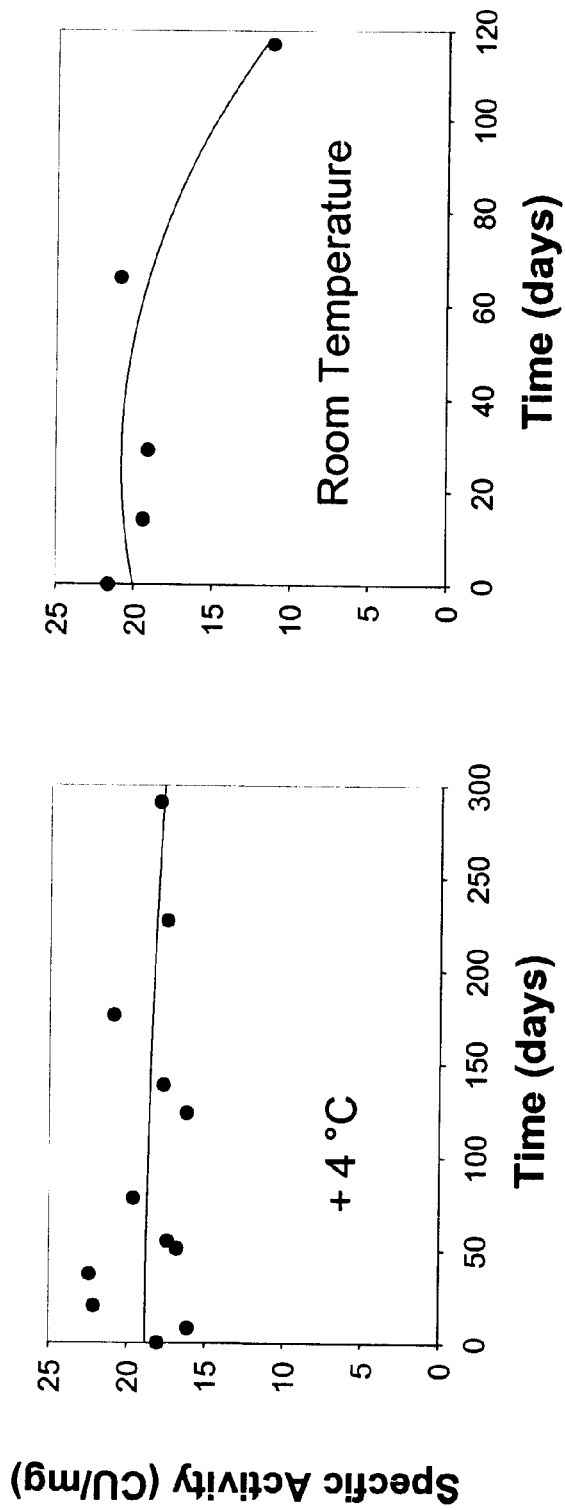
Figure 2. Plasmin stability in acidified water (pH 3.7) as measured by the caseinolytic assay. Left panel - at 4°C, right panel - at room temperature

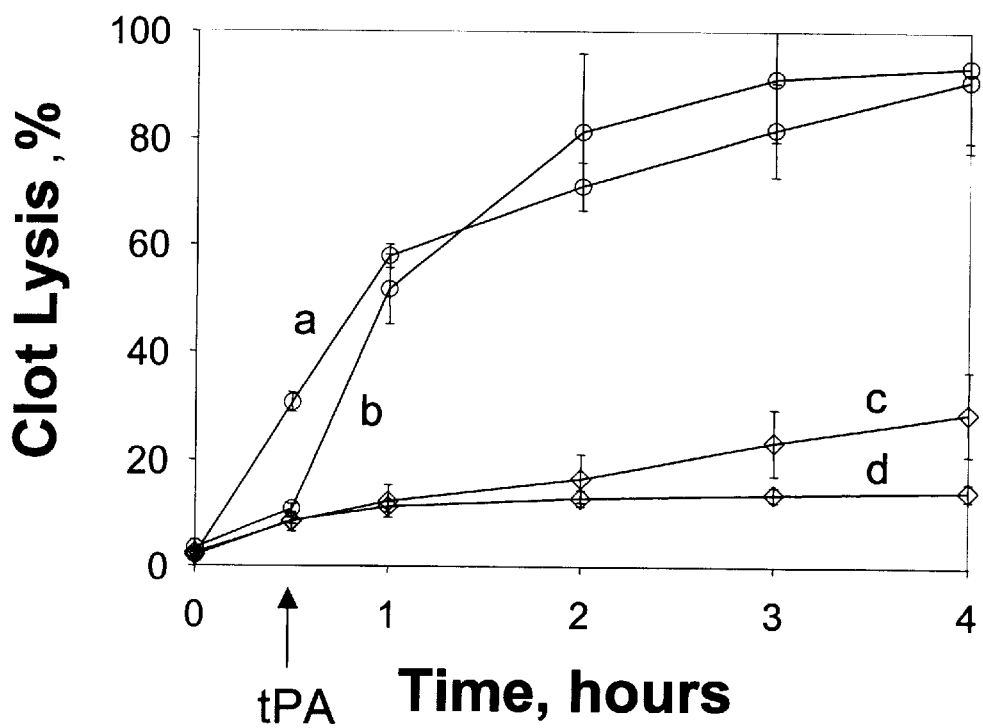
Figure 3. Fibrin clot lysis in PBS with: a - 0.3 mg of purified plasmin; b - 0.3 mg of Lys-plasminogen + 0.1 µg of tPA; c - 0.1 µg of tPA; d - buffer as a control

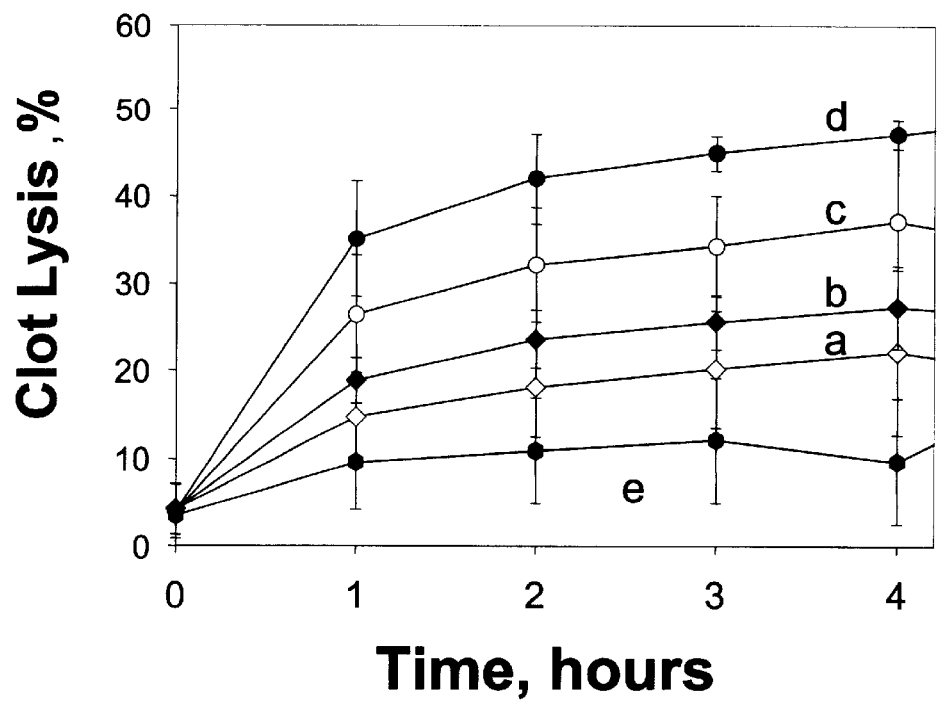
Figure 4. Thrombolytic potency of active plasmin. Increasing amounts of plasmin were added to $I^{125}$ fibrin-labeled plasma clots and the degree of thrombolysis was assessed by measuring the release of the radioactivity into plasma surrounding the clot. a - 0.15 mg/ml of plasmin in the reaction tube, b - 0.30 mg/ml; c - 0.45 mg/ml; d - 0.60 mg/ml; e- control with no plasmin added.

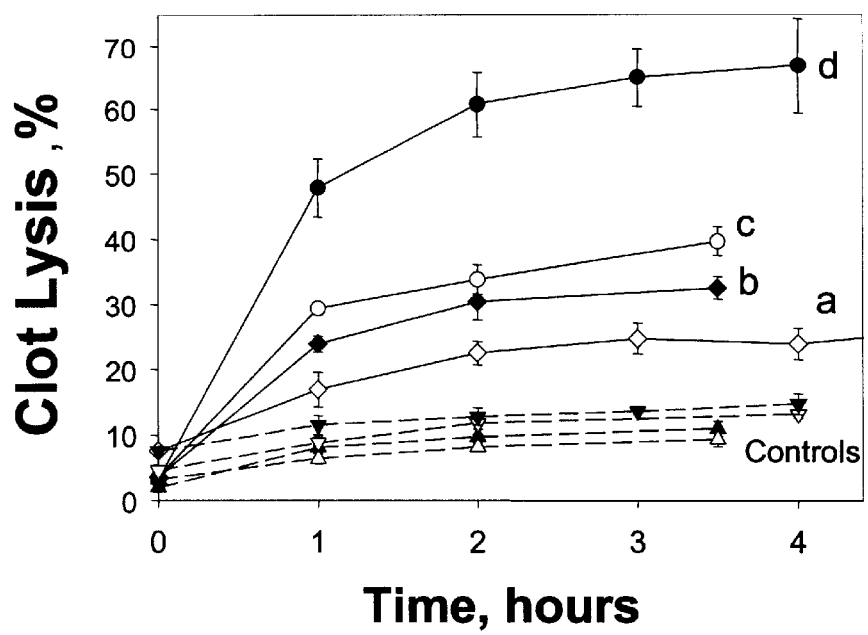
Figure 5. Effect of plasma inhibitors on plasmin induced thrombolysis as measured by the $I^{125}$ radio-labeled clot lysis assay. Clot lysis was conducted in: a) - normal plasma; b) - $\alpha_2$-macroglobulin inactivated plasma; c) - $\alpha_2$-antiplasmin deficient plasma; d) - in PBS.

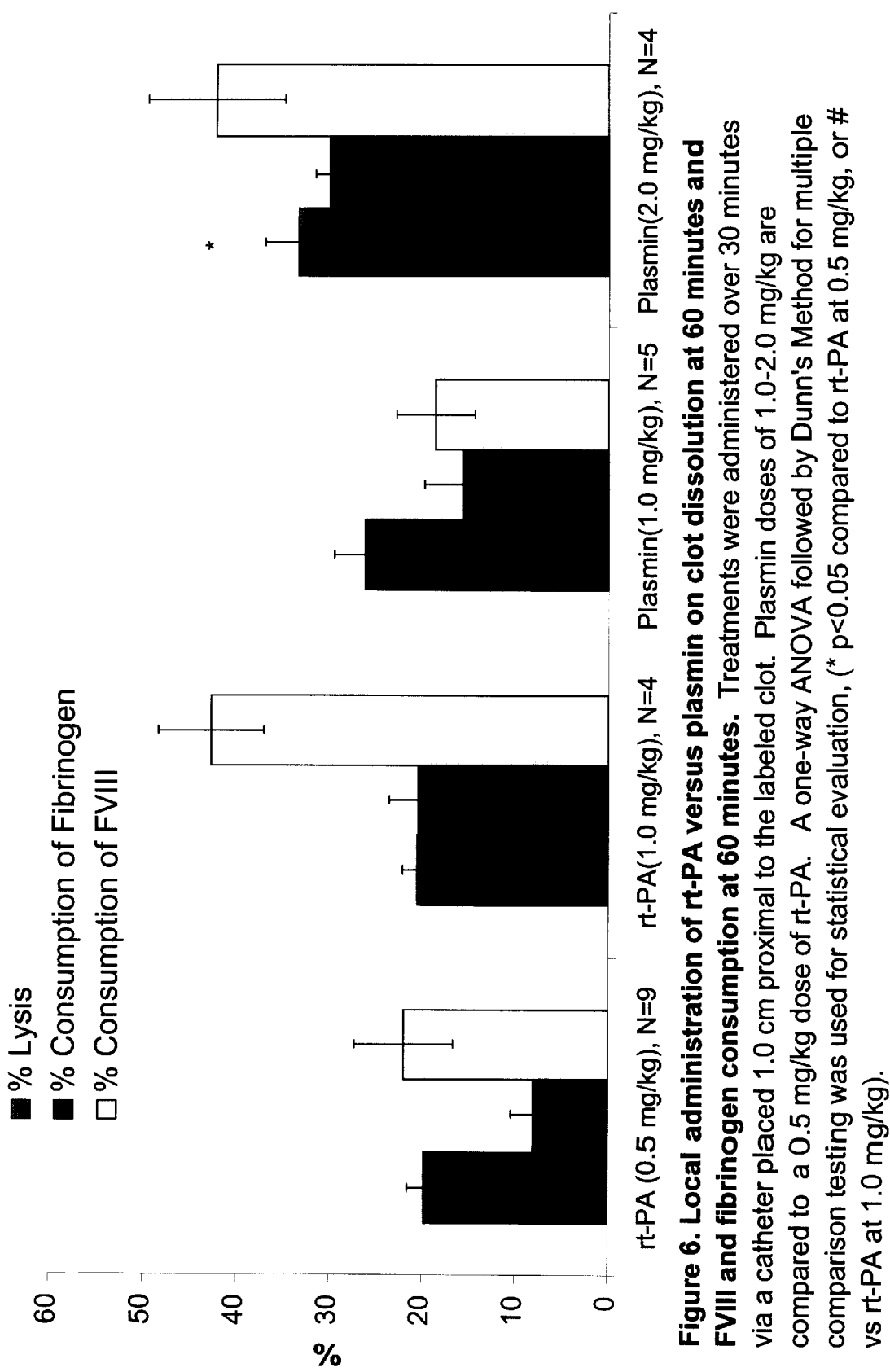

Figure 6. Local administration of rt-PA versus plasmin on clot dissolution at 60 minutes and FVIII and fibrinogen consumption at 60 minutes. Treatments were administered over 30 minutes via a catheter placed 1.0 cm proximal to the labeled clot. Plasmin doses of 1.0-2.0 mg/kg are compared to a 0.5 mg/kg dose of rt-PA. A one-way ANOVA followed by Dunn's Method for multiple comparison testing was used for statistical evaluation, (* $p<0.05$ compared to rt-PA at 0.5 mg/kg, or # vs rt-PA at 1.0 mg/kg).

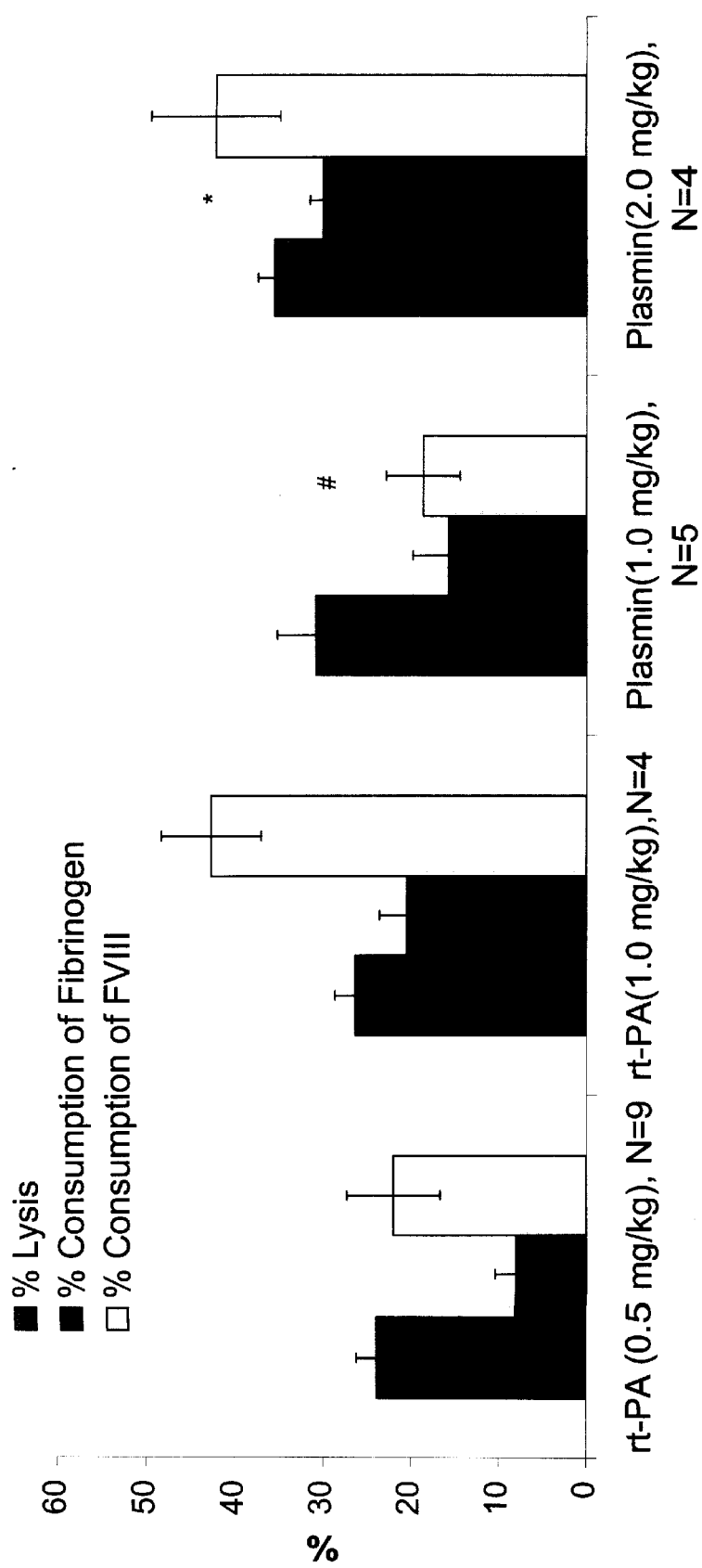
Figure 7. Local administration of rt-PA versus plasmin on clot dissolution at 90 minutes and FVIII and fibrinogen consumption at 60 minutes. Treatments were administered over 30 minutes via a catheter placed 1.0 cm proximal to the labeled clot. *Significantly different (p < 0.5) from tPA at 0.5 mg/kg.

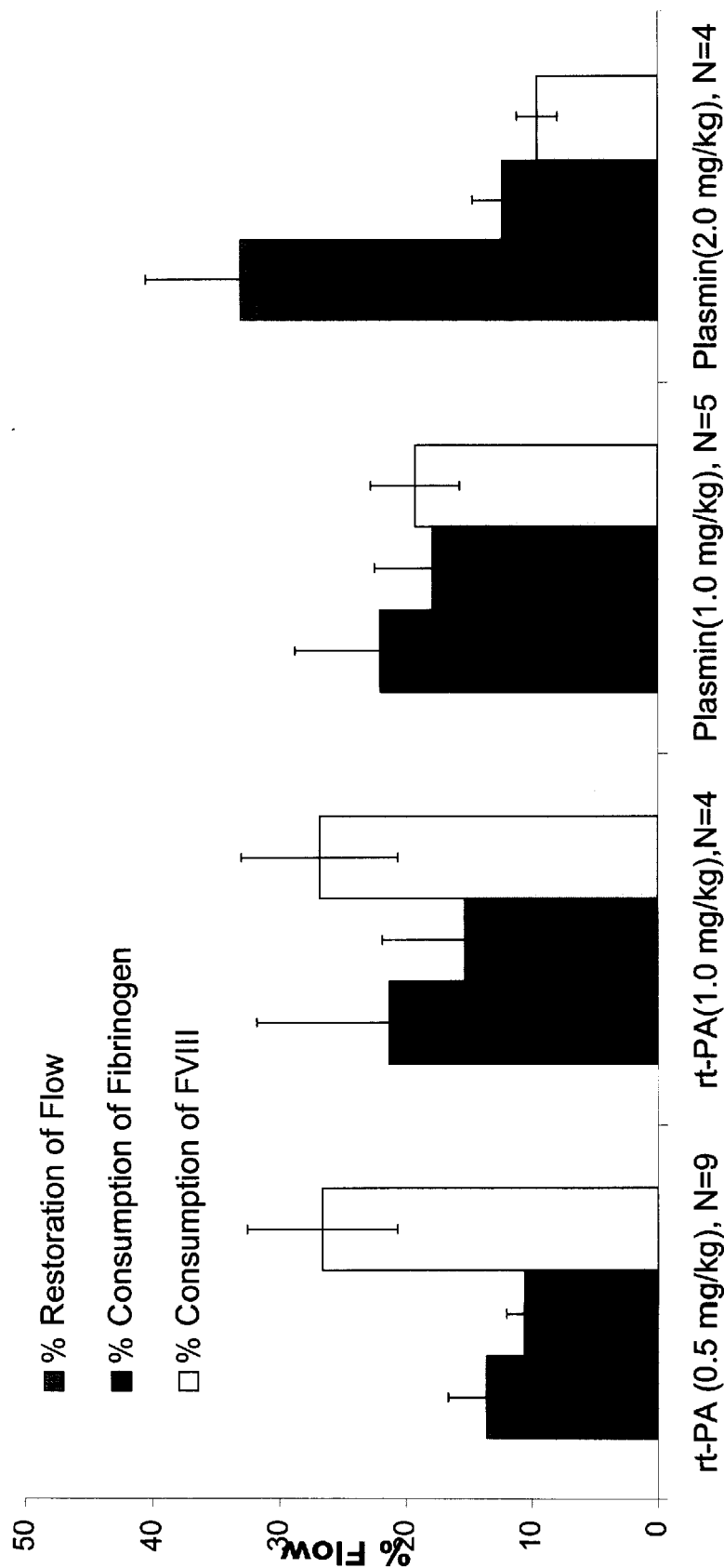
Figure 8. Effect of local administration of tPA and plasmin on flow restoration at 60 min and Factor VIII and fibrinogen consumption at 60 min.

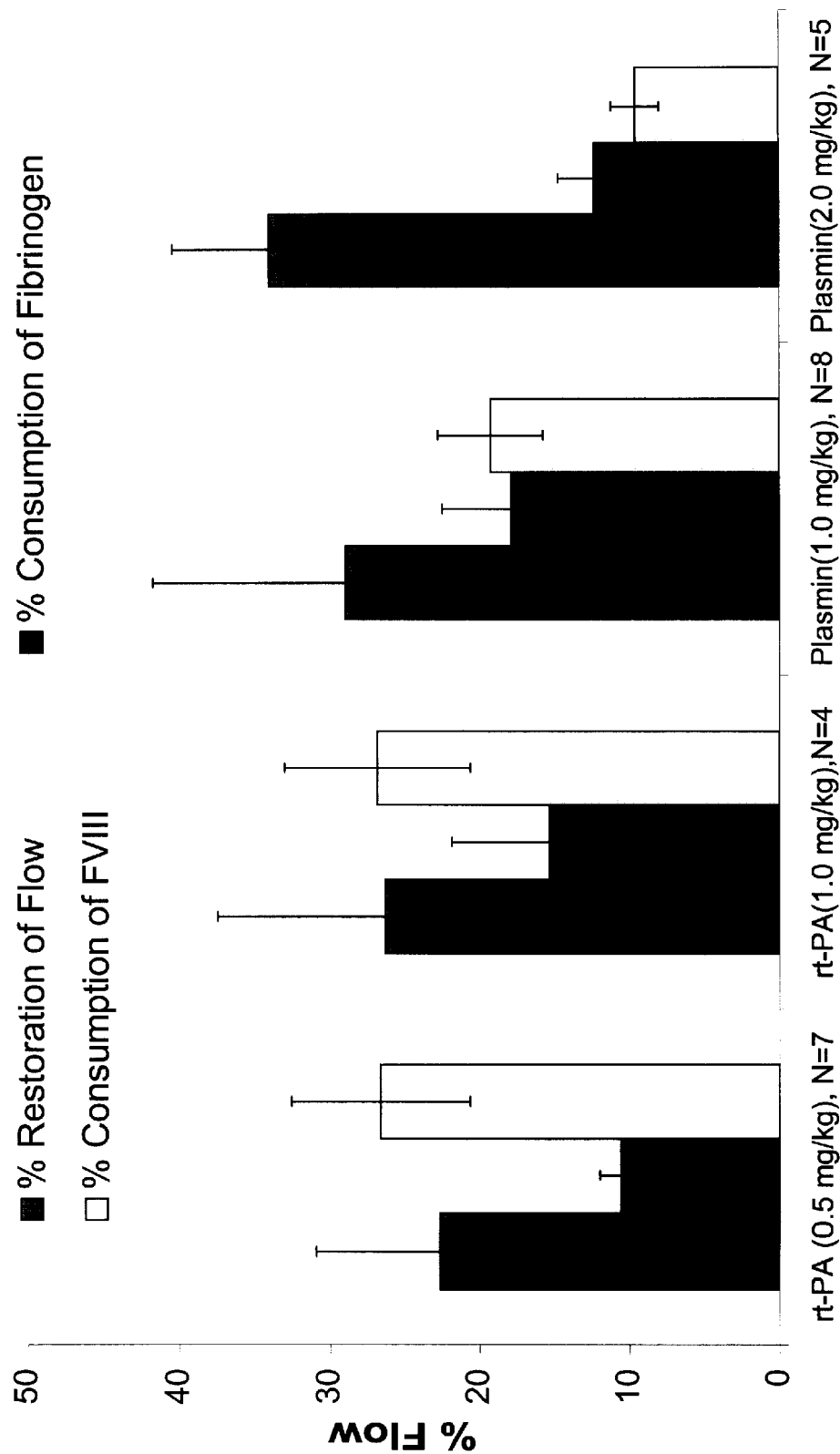
Figure 9. Effect of local administration of tPA and plasmin on flow restoration at 90 min and Factor VIII and fibrinogen consumption at 60 min.

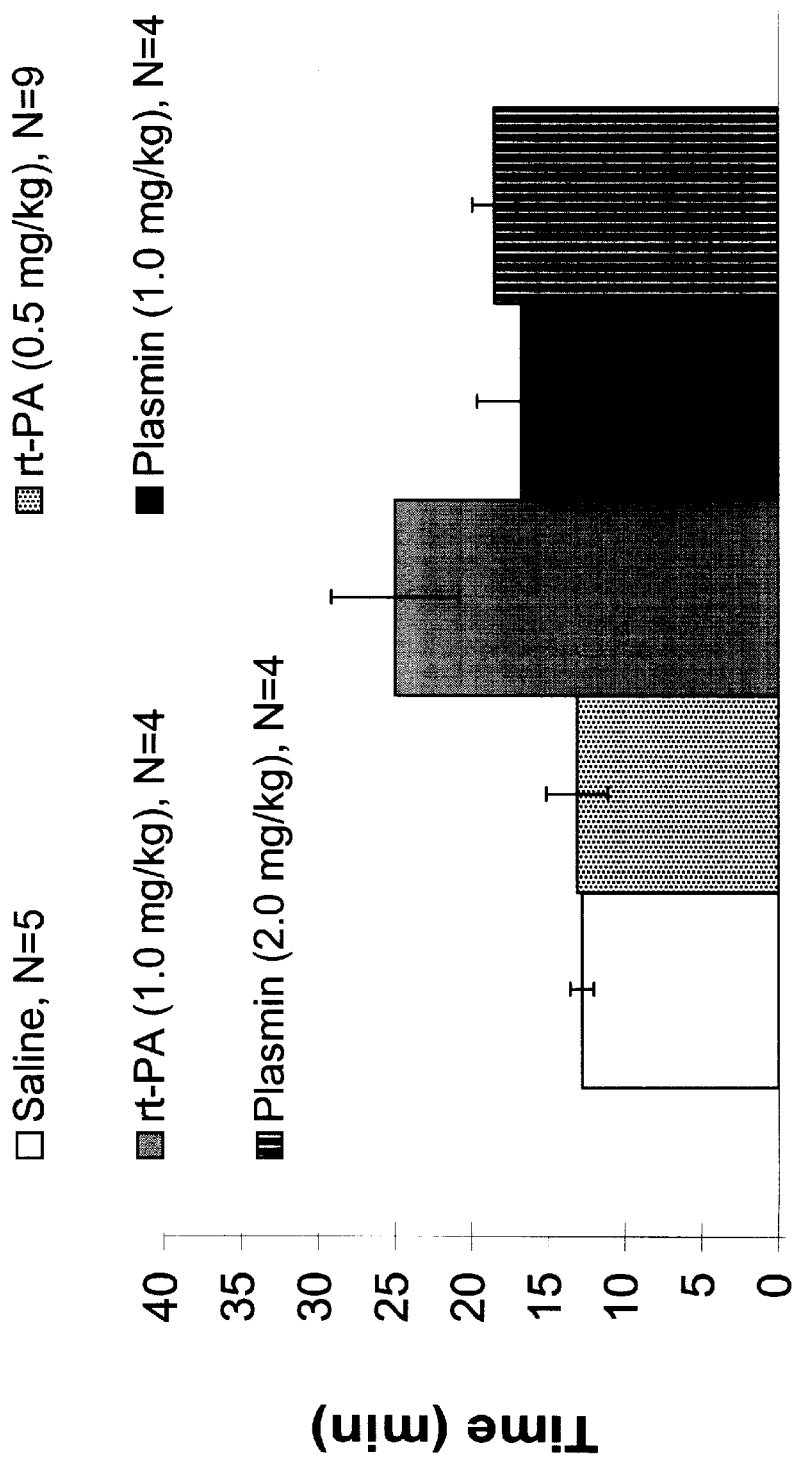
Figure 10. Local administration of rt-PA versus plasmin on cuticle bleed times. Cuticle bleed times were measured by clipping the apex of the cuticle. Two cuticles, on different feet, were clipped, averaged and presented as mean +/- SEM

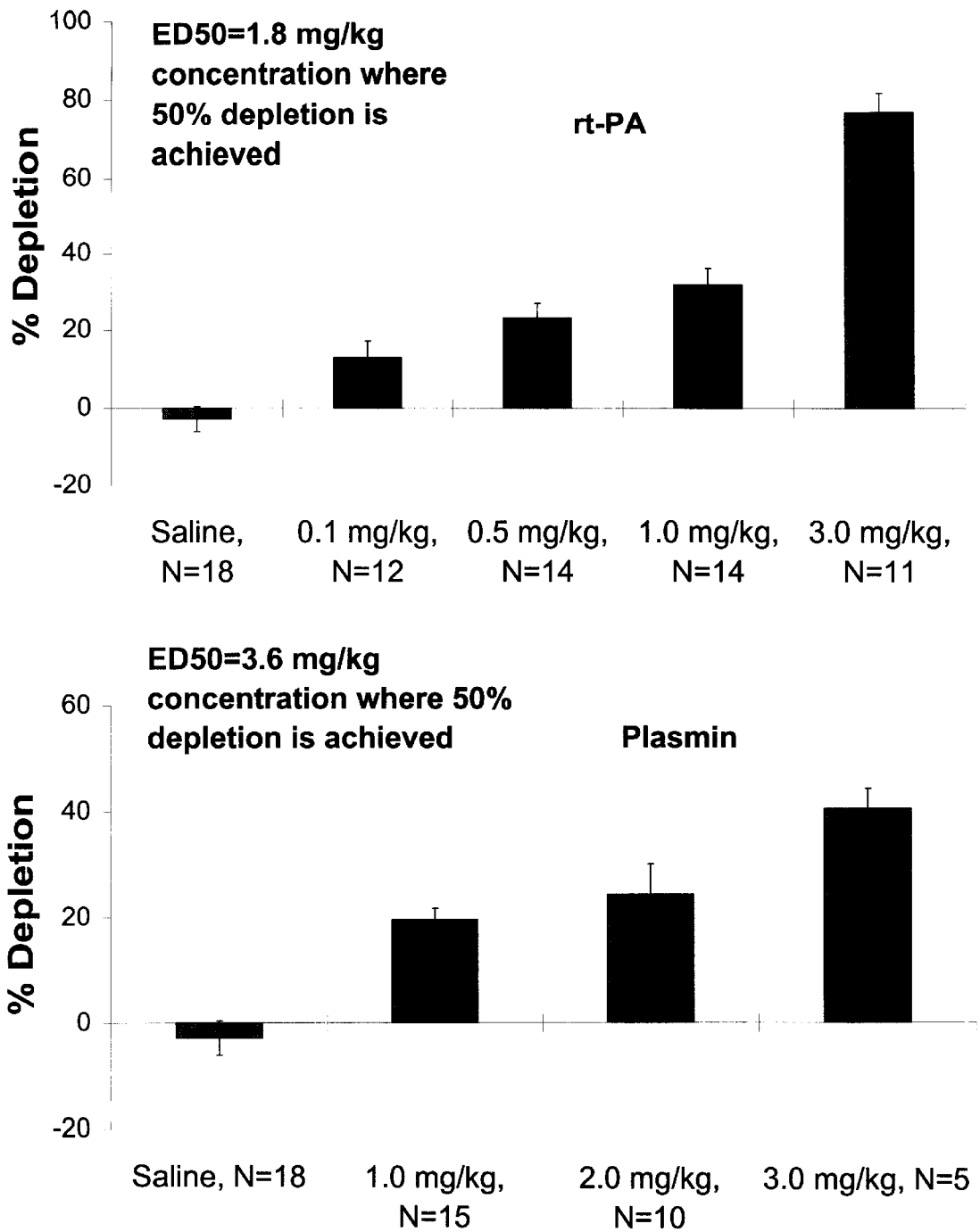
Figure 11. Effect of increasing doses of t-PA and Plasmin on Factor VIII depletion

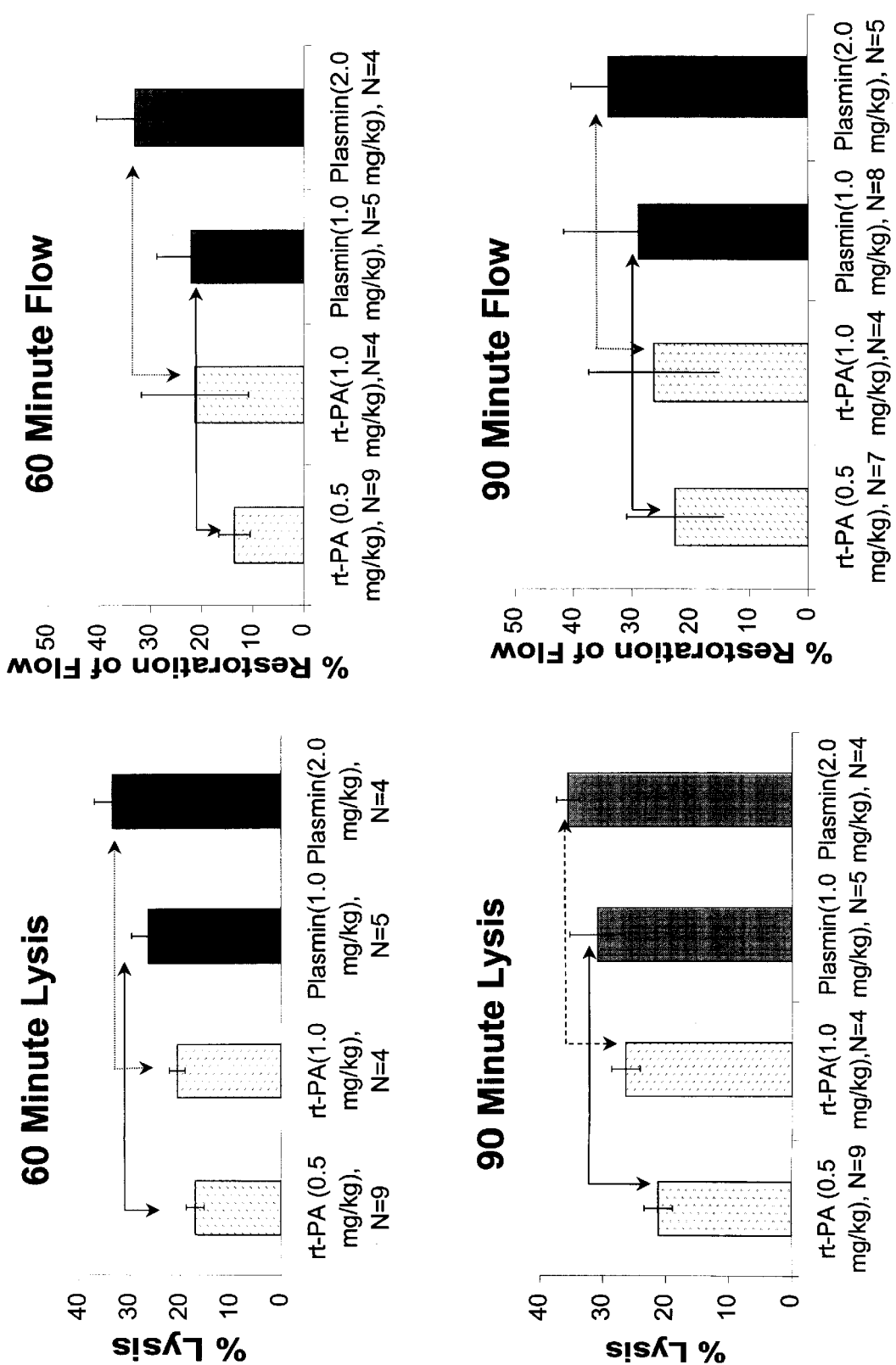
Figure 12. Risk/benefit evaluation of plasmin versus t-PA. Arrows denote equivalent risk profile.

METHOD OF THROMBOLYSIS BY LOCAL DELIVERY OF ACTIVE PLASMIN

BACKGROUND OF THE INVENTION

1. Field

The invention is related to thrombolytic therapy with the plasmin, specifically by local delivery of active plasmin proximal to or directly at the clot site. This therapeutic method is particularly applicable to the dissolution of clots wherever catheter directed delivery is feasible, particularly for example in distal limbs (e.g. arms and legs).

2. Background

Plasmin, the principle fibrinolytic enzyme in mammals, is a serine protease with trypsin-like specificity. It derives from the inactive precursor plasminogen which circulates in plasma at a concentration of ~1.5 µM. Plasminogen activators such as tPA or urokinase cleave a single-chain plasminogen molecule at the $Arg^{560}$-$Val^{561}$ peptide bond, producing active plasmin. The resulting two chains of plasmin are held together by two interchain disulphide bridges. The light chain (25 kDa) carries the catalytic center and is homologous to trypsin and other serine proteases. The heavy chain (60 kDa) consists of five very homologous triple-loop structures called kringles. Some kringles contain the so called lysine-binding sites which are responsible for plasminogen/plasmin interaction with fibrin, $a_2$-antiplasmin and other proteins.

In spite of the success of thrombolytic drugs such as tissue plasminogen activator (tPA), streptokinase and urokinase, various thrombotic disorders, including myocardial infarction, occlusive stroke, deep venous thrombosis and peripheral arterial disease, remain a serious clinical problem. It appears that the currently available thrombolytic agents have several important limitations. At best, TIMI flow 3 within 90 min is obtained in approximately 50% of patients, acute coronary reocclusion occurs in roughly 10% of patients, coronary recanalization requires on average 45 minutes or more, intracerebral bleedings occurs in 0.3% to 0.7% of patients, and the residual mortality is at least 50% of that without thrombolytic treatment. Therefore, it is not surprising that research in the area of thrombolytics has focused on improvement of the existing plasminogen activators and finding new ones in an attempt to improve their fibrin specificity and increase plasma half-life to allow bolus administration.

The focus of development has been new plasminogen activators and with the exception of novel plasminogen activator (nPA), they all exhibit better fibrin specificity. They preserve the circulating levels of fibrinogen, plasminogen, $a_2$-antiplasmin, Factors VIII and V. Nevertheless, based on the results of Phase II clinical trials with TNK-tPA and nPA, the improved safety profile of the new plasminogen activators has not translated into the better clinical outcome following thrombolytic therapy. The percentage of moderate and major bleeding episodes, including intracranial hemorrhage and stroke, were comparable with original tPA. The clogged arteries were not opened earlier and the rate of re-occlusions remains unchanged. It appears that the only benefit these activators have is the prolonged plasma half-life and the possibility of bolus administration.

An abstract on the method of treatment provided herein was published in BLOOD, Journal of the American Society of Hematology, Nov. 15, 1998, Abstract 3400. The abstract disclosed the potential of active Plasmin as a thrombolytic agent with the shift in modern fibronolytic treatment from systemic to local delivery.

U.S. Pat. No. 5,288,489 assigned to Orion Therapeutic Systems, Inc. discloses a fibrinolysis and fibrinogenolysis treatment which includes parenterally introducing into the body of a human patient human plasmin in fibrinolytically and fibrinogenolytically active form at a concentration and for a time sufficient to permit fibrinolytically and fibrinogenolytically active human plasmin to reach a concentration about the site of an intravascular clot sufficient to lyse the clot and/or to reduce circulating fibrinogen levels. This patent discloses the generation of plasmin from plasminogen just prior to its introduction into the body. The plasminogen is activated, or an plasmin inhibitor is removed, just prior to administration.

SUMMARY OF THE INVENTION

This invention relates to the discovery that thrombolytic therapy can be improved by the administration of active plasmin directly at or proximal to the site of a clot. Plasmin autodegrades and has not been available for therapeutic administration. This invention provides a method of preparing active plasmin for such direct administration. Plasmin is obtained by isolating plasminogen from Cohn Fraction II & II, activating the plasminogen obtained to plasmin and isolating the plasmin in an aqueous solution having a pH of less than about 4 to provide a stable formulation of plasmin. Plasminogen may be activated by using a plasminogen activator, such as urokinase, bound to an affinity resin column, preferably a urokinase-sepharose column. The active plasmin may then be captured on a benzamidine affinity resin, preferably a benzamidine-Sepharose column, and finally eluted with a low pH buffer. The eluted plasmin is formulated in an aqueous solution, acidified to a pH of less than about 4, preferably, about 3.7. The aqueous plasmin solution may be lyophilized and is substantially free of plasminogen activator. No extensive manipulation is required to administer this formulation. Proof is provided herein that this is a viable therapy compared to the current use of plasminogen activators that can cause extraneous bleeding along with dissolution of a clot.

BRIEF DESCRIPTION OF THE FIGURES

FIG. 1 shows the pH dependence of plasmin activity as measured with chromogenic substrate S2251.

FIG. 2 shows plasmin stability in acidified water (pH 3.7) as measured by caseinolytic assay. [Left panel at 4 degrees centigrade; right panel at room temperature].

FIG. 3 shows fibrin clot lysis in PBS with: a—0.3 mg of purified plasmin; b—0.3 mg of Lys-plasminogen+0.1 micrograms of tPA; c—0.1 micrograms of tPA; d—buffer as a control.

FIG. 4 shows thrombolytic potency of active plasmin. Increasing amounts of plasmin were added to $I^{125}$ fibrin-labeled plasma clots and the degree of thrombolysis was assessed by measuring the release of the radioactivity into plasma surrounding the clot. a—0.15 mg/ml of plasmin in the reaction tube, b—0.30 mg/ml; c—0.45 mg/ml; d—0.60 mg/ml; e—control with no plasmin added.

FIG. 5 shows the effect of plasma inhibitors on plasmin induced thrombolysis as measured by the $I^{125}$ radio-labeled clot lysis assay. Clot lysis was conducted in: a)—normal plasma; b)—$a_2$-macroglobulin inactivated plasma; c)—$a_2$-antiplasmin deficient plasma; d)—in PBS.

FIG. 6 shows local administration of rt-PA versus plasmin on clot dissolution at 60 minutes and FVIII and fibrinogen consumption at 60 min. Treatments were administered over 30 minutes via a catheter placed 1.0 cm proximal to the labeled clot. Plasmin doses 1.0–2.0 mg/kg are compared to a 0.5 mg/kg dose of rt-PA. A one-way ANOVA followed by Dunn's method for multiple comparison testing was used for statistical evaluation, (*p<0.05 compared to rt-PA at 0.5 mg/kg, or # vs rt-PA at 1.0 mg/kg).

FIG. 7 shows local administration of rt-PA versus plasmin on clot dissolution at 90 minutes and FVIII and fibrinogen consumption at 60 minutes. Treatments were administered over 30 min via catheter placed 1.0 cm proximal to the labeled clot.* Significantly different (p<0.5) from tPA at 0.5 mg/kg.

FIG. 8 shows effect of local administration of tPA and plasmin on flow restoration at 60 min and Factor VIII and fibrinogen consumption at 60 min.

FIG. 9 shows effect of local administration of tPA and plasmin on flow restoration at 90 min and Factor VIII and fibrinogen consumption at 60 min.

FIG. 10 shows local administration of rt-PA versus plasmin on cuticle bleed times. Cuticle bleed times were measured by clipping the apex the cuticle. Two cuticles, on different feet, were clipped, averaged and presented as mean+/−SEM.

FIG. 11 shows effect of increasing doses of t-PA and Plasmin on Factor VIII depletion.

FIG. 12 shows risk/benefit evaluation of plasmin versus t-PA. Arrows denote equivalent risk profile.

BRIEF DESCRIPTION OF THE INVENTION

With the escalating use of arterial and venous catheters in the clinics, locally delivered active plasmin offers an attractive therapeutic opportunity in thrombolytic therapy or opening clogged catheters. There are a number of reasons for this: 1) Being an active serine protease, plasmin is a direct clot dissolving agent in contrast to plasminogen activators, which require the presence of the substrate (plasminogen) in the vicinity of the clot; 2) Local catheter directed thrombolytic therapy with active plasmin can be intensified to whatever level is required to achieve completeness of clot lysis; 3) Plasmin also has the theoretical potential to be a safer thrombolytic because the lower dosage required for local delivery may decrease or even eliminate bleeding complications associated with high dose thrombolytic therapy and any potential spillage of plasmin activity from the immediate vicinity of the thrombus site will be quickly neutralized by circulating á$_2$-antiplasmin.

There are several technical challenges associated with plasmin purification, especially with its therapeutic use and delivery. Plasmin is an active serine protease which is prone to autodigestion and inactivation at physiological pH. Unfortunately, plasmin degradation is most noticeable in the pH range required for manifestation of its function, clot lysis. These problems have been successfully circumvented by the plasmin purification and formulation disclosed. The essential features of this purification strategy are affinity chromatography on benzamidine-Sepharose with subsequent elution of active plasmin with an acidic buffer and its formulation in acidified water. This approach provided consistently highly pure and active plasmin. Its efficacy was demonstrated both in the in vitro assays and in an in vivo rabbit jugular vein thrombolysis model. Using these assay systems it was demonstrated that catheter-delivered plasmin infusion is comparable, if not superior to tPA, in its thrombolytic efficacy and safety profile.

One limitation of current thrombolytic therapy with plasminogen activators is substrate (i.e. plasminogen) availability in the vicinity of the clot. With segments of current fibrinolytic treatment regimens shifting from systemic to local delivery, active plasmin could be used therapeutically as a potent thrombolytic agent. In contrast to various plasminogen activators which are currently used as thrombolytics, direct, local thrombolytic therapy with active plasmin can be intensified to whatever level is required to achieve clot lysis because plasmin acts directly upon the fibrin polymer. Also, plasmin has the potential to be a safer thrombolytic because: 1) the lower dosage required for local delivery may lessen bleeding associated with thrombolytic therapy; and 2) any potential spillage of plasmin activity from the thrombus site is quickly neutralized by circulating $\alpha_2$-antiplasmin.

Highly pure, active plasmin was prepared from plasminogen that had been purified from Cohn Fraction II+III paste. The purity of plasmin was greater than 95%, and specific activity was in the range of 21–23 CU/mg. The plasmin preparations did not contain free urokinase, which was used in an immobilized form for conversion of plasminogen into plasmin.

By means of an in vitro $^{125}$I-fibrin-labeled clot lysis assay, it was shown that plasmin was capable of dissolving plasma clots in a dose-dependent manner. Fibrinolysis was enhanced by deletion of either $\alpha_2$-antiplasmin or $\alpha_2$-macroglobulin in plasma surrounding the clot, and even more so by the deletion of all inhibitors (i.e., in PBS). These results indicate that clot lysis by plasmin is under very strict physiologic control by the endogenous plasma plasmin inhibitors, thus providing a basis for safer thrombolytic therapy.

The in vivo efficacy of plasmin (1–2 mg/kg) administered locally via a catheter was compared with that of tPA (0.5 and 1.0 mg/kg) in the rabbit jugular vein thrombosis model. Two approaches were used to assess clot lysis: 1) real time measurements of % lysis with a radio-labeled clot; and 2) restoration of baseline blood flow via application of a flow probe and flow meter. The rate of clot lysis was monitored and quantitated over 90 min by placement of a gamma counter directly over a $^{125}$I-fibrin-labeled clot. Concomitantly, the consumption of factor VIII and fibrinogen, as well as cuticle bleeding time (CBT), were measured as indicators of the systemic lytic state. Either plasmin or tPA (total volume 10 ml) was infused over 30 min via a catheter placed ~1 cm proximal to the clot. An equal volume of saline served as a control. In comparison with tPA (0.5–1.0 mg/kg), plasmin (1.0–2.0 mg/kg) infused locally induced comparable or significantly better clot lysis, with similar or less consumption of Factor VIII and fibrinogen and CBT. Risk/benefit evaluation of plasmin treatment revealed that twice the dose of plasmin (wt basis) induced similar bleeding side effects as tPA.

The invention disclosed herein is that active plasmin can be effectively and safely used as a thrombolytic agent during catheter-assisted local thrombolysis. Plasmin has comparable, if not superior, lytic activity compared to tPA, and the safety profile appears similar in this animal model of local thrombolytic delivery.

MATERIALS AND METHODS

Proteins and Chemicals

Plasminogen was purified from Fraction II+III paste by affinity chromatography on Lys-Sepharose [Deutsch, D. G. and Mertz, E. T. (1970) Plasminogen: purification from human plasma by affinity chromatography. *Science* 170, 1095–1096]. 200 g of the paste was resuspended with 2 L of 0.15M sodium citrate buffer, pH 7.8. The suspension was incubated overnight at 4° C., centrifuged at 14000 rpm, filtered through fiberglass and mixed with 500 ml of Lys-Sepharose 4B (Pharmacia). Binding of plasminogen occurred at room temperature for 2 h. Lys-Sepharose was than transferred onto a 2 l glass filter, washed several times with 0.15M sodium citrate+0.3M NaCl until the OD dropped below 0.05. Bound plasminogen was eluted with three 200 ml portions of 0.2M ε-aminocaproic acid. Eluted plasminogen was precipitated with solid ammonium sulfate (0.4 g per 1 ml of plasminogen solution). This ammonium sulfate precipitate of crude (80–85% pure) plasminogen was stored at 4° C. and served as a source for plasmin purification.

Low molecular weight urokinase Abbokinase (obtained from Abbott Laboratories, Chicago Ill.) was further purified by affinity chromatography on Benzamidine-Sepharose. Urokinase was coupled to CNBr-activated Sepharose 4B as described in the Pharmacia brochure. 1.3 mg of LMW-urokinase in 50 mM acetate buffer, pH 4.5 was diluted with 5 ml of the coupling buffer, 0.1M sodium bicarbonate, pH 8.0. This solution was immediately combined with 5 ml of CNBr-activated Sepharose which was previously swollen and washed in 0.1M HCl. The coupling occurred for 4 hr on ice bath on a bench-top shaker. The excess of active group was blocked with 0.1M-Tris, pH 8.0. Each batch of urokinase-Sepharose was used 5 times and stored in 50% glycerol in water at 4° C. between the cycles.

tPA (Activase) was from Genentech. Fibrinogen (plasminogen free) and α-thrombin (3793 U/ml) were purchased from Enzyme Research, Inc. $\alpha_2$-antiplasmin was obtained from Athens Research Technologies. Commercially available plasmin was purchased from Heamotologic Technologies, Inc. Chromogenic plasmin substrate S2251 was from Chromogenix. $^{125}$I-Labeled human fibrinogen (150–250 μCi/mg) was from Amersham Pharmacia Biotech. Casein for determination of plasminoge/plasmin activity, pre-made 10×PBS, Tris, and lysine were from Sigma Chemicals, St. Louis, Mo. All other chemicals were of reagent grade or higher.

SDS-polyacrylamide gel electrophoresis was performed in the Pharmacia Phast System apparatus using pre-made 8–25% gradient gels and SDS-buffer strips.

Plasmin specific activity was measured using an adapted caseinolytic assay for plasminogen [Robbins, K. C. and Summaria, L (1970) Human Plasminogen and Plasmin. *Meth. Enzymology*, 19:257–273]. Briefly, 1 ml of 4% casein solution in the same buffer and an appropriate volume of 67 mM sodium phosphate buffer, pH 7.4 was added to a test polycarbonate tube. The solutions were vortexed and incubated at 37° C. for 10 minutes. Plasmin samples or buffer (=Blank) were added to each tube at 15 second intervals, mixed thoroughly and incubated at 37° C. for 30 minutes. The reaction was stopped with the addition of 3 ml of 15% trichloroacetic acid and allowed to precipitate for 15 minutes. The tubes were centrifuged in a tabletop centrifuge at 3200 rpm for 20 minutes. The supernatant was transferred to plastic cuvettes and the $A_{280}$ of each sample was determined. The specific caseinolytic activity of each sample was determined by the following formula:

$$\frac{[A_{280}(\text{Plasmin Sample}) - A_{280}(\text{Blank})]3.27}{\mu g\, Pm \text{ in assay}} = CU/mg$$

Each plasmin sample was tested in duplicate.

$^{125}$I-Fibrin Labeled Clot Lysis Assay.

The fibrinolytic properties of plasmin were determined in an in vitro system consisting of a radiolabeled plasma clot immersed in human citrated plasma [Lijnen, H. R., Zamarron, C., Blaber, M., Winkler, M. E. and Collen, D. (1986) Activation of plasminogen by pro-urokinase. *J.Biol.Chem.* 261, 1253–1258]. Plasma used in all experiments was Bayer single donor plasma which was thawed at 37° C., aliquoted (25 to 50 ml), re-frozen and stored at –80° C. The stock solution of $^{125}$I-labeled fibrinogen was prepared by rehydrating the contents of the vial (approximately 110 μCi/vial) with 1.0 ml of 0.15 M sodium citrate and was stored at 4° C. The following experimental protocol was utilized. Ten μ of $^{125}$I fibrinogen was added to a polycarbonate test tube containing 250 μl of plasma at 37° C. and mixed briefly. Twenty five μl of α-thrombin, diluted with 0.1M $CaCl_2$ to a final concentration of 10–20 U/ml, was added to the plasma and mixed again. The radio-labeled clots were allowed to age for five minutes at 37° C. and then washed gently with PBS. The clots were transferred into test tubes containing 2.25 ml plasma or buffer, one clot per tube. A baseline radioactivity sample was measured for each clot. Plasmin was added to each tube, where indicated, after the addition of each clot. The clots were returned to 37° C. for the duration of the experiment. Further samples were taken at indicated time points for measurement of released radioactivity. The extent of thrombolysis was calculated from the ratio between the amount of radioactivity released from the clot into the plasma and the total amount of radioactivity in the reaction tube. The release of $^{125}$I-labeled fibrin degradation products, expressed in percent, was plotted versus time.

In addition to the plasma milieu, some clot lysis experiments were conducted in a buffer environment or with plasma lacking $\alpha_2$-antiplasmin or $\alpha_2$-macroglobulin activity. $\alpha_2$-Antiplasmin-depleted plasma was obtained by passing normal plasma through Kringles1-3-Sepharose [Wiman, B. Affinty-chromatographic purification of human alpha 2-antiplasmin (1980) *Biochemical Journal*. 191(1):229–32]. $\alpha_2$-Macroglobulin-inactivated plasma was obtained by treatment of normal plasma with 0.1M methylamine [Barrett, A. J, Brown, M. A., Sayers, C. A. (1979) The electophoretically "Slow" and "Fast" forms of the $\alpha_2$-macroglobulin molecule, 181: 401–418] for 2 hr at 37° C. with subsequent dialysis against PBS at 4° C.

Rabbit Jugular Vein Thrombosis Model.

In order to determine the in vivo efficacy and safety of locally administered lys-plasmin we utilized the rabbit jugular vein thrombosis model [Collen, D., Stassen, J M., Verstraete, M., (1983) Thrombolysis with human extrinsic (tissue-type) plasminogen activator in rabbits with experimental jugular vein thrombosis. Effect of molecular form and dose of activator, age of the thrombus, and route of administration. J. of Clin. Invest. 71(2):368–376]. This is a well characterized and accepted thrombolysis model which was used to characterize and develop recombinant tPA and continues to be used to evaluate the pharmacological profile of new thrombolytic agents. The model, in brief was as follows: Rabbits (2–3 kg) are sedated with ketamine/xylazine and a 22 G venous catheter is placed in the ear vein for administration of a dilute solution of pentobarbital (5–10 mg/kg/hr). The neck is shaved and an arterial catheter is placed in the carotid artery for pressure measurements and blood sampling. A tracheotomy is performed for placement of a tracheal tube to facilitate breathing. The jugular vein is carefully isolated with blunt dissection up to and including the facial vein. A 24 G catheter is placed in the facial vein and the jugular vein is clamped both distal and proximal to the isolated facial vein. The isolated vein segment is washed several times with saline and completely drained of blood. The isolated segment is washed several times with a thrombin solution (500 IU/ml, Bayer Corp.). Following the last wash, 0.5 ml of arterial blood sample is drawn from the arterial catheter and mixed quickly with 50 μl of $I^{125}$ labeled fibrinogen (approximately 1 μCi). The mixture is rapidly infused into the isolated vein segment via the facial vein until the vein segment is fully distended. The clot is mixed by massaging the vein with forceps and a piece of Saran Wrap is placed over the exposed jugular vein to prevent it from drying out. Heparin (100 IU/kg) is administered to prevent deposition of cold fibrinogen on clot. The clot is allowed to age for 30 minutes and clips are removed. The stability of the clot is monitored over a 30 minute equilibration period. Dissolution of the labeled clot (% lysis) is monitored continuously with a G1LE gamma counter probe placed directly over the clot. In order to provide a physiologic readout of clot dissolution, in a separate series of experiments blood flow restoration was used as another index of clot lysis. In these experiments, an appropriate sized flow probe was placed distal to the occlusive clot (not labeled) ) connected to a Transonic Flowmeter and venous blood flow measurements were taken every 15 minutes. Baseline blood flow before clot formation was 12–18 ml/min and data is represented as % of baseline.

For these local administration studies, a catheter (PE 50) was advanced via the marginal ear vein, to within 1 cm of the obstructive clot. We used two doses of tPA; 0.5 and 1.0 mg/kg and two doses of plasmin; 1.0 mg/kg and 2 mg/kg. Previous dose-response studies determined that these were optimal doses i.e., maximal lysis without severe consumption of coagulation factors and bleeding. These doses were contained in 10.0 ml total volume infused over 30 minutes. We measured % lysis at 60 and 90 minutes with the radiolabeled clot and, in another separate series of experiments with unlabeled clots, % restoration of flow was measured at similar time points. Arterial blood samples (4 ml) obtained at 0 and 60 minutes were used for determination of fibrinogen and factor VIII levels Fibrinogen concentration were determined using a MLA Electra 800 Coagulation Timer and the Fibrinogen Assay Set. Factor VIII levels were determined by the COATEST VIII:C4 assay using human Factor VIII to generate a standard curve. Cuticle bleeding times at 0 and 60 minutes were determined by clipping the rabbit's nail, at the apex, with a dog nail trimmer. The blood was dabbed, without touching the nail, with a filter paper every two minutes until a clot formed and the filter patper did not wick blood away. Results are presented as mean±SEM and to evaluate significant differences between groups, a one-way ANOVA followed by Bonferroni's procedure for multiple-comparison testing was used. $P<0.05$ was considered significant.

RESULTS AND DISCUSSION
Purification and Characterization

Any strategy for plasmin purification must account for the following factors. The purification protocol should be simple, effective, reproducible and robust. It should be able to produce sufficient amount of highly pure plasmin with activity comparable with potential activity of purified plasminogen preparations. The purification should at least preserve the plasmin activity, if not enrich it. The final plasmin should not be contaminated with plasminogen activators since their presence is undesirable for therapeutic use. To satisfy all the above criteria, the purification method disclosed herein includes the following 4 major steps:

Step 1: Activation of plasminogen to plasmin using Urokinase-Sepharose;
Step 2: Capturing of active plasmin on Benzamidine-Sepharose;
Step 3: Elution of the bound plasmin with low pH buffer;
Step 4: Formulation of final plasmin in acidified to pH 3.7 water.

1. Activation of Plasminogen to Plasmin Using Urokinase-Sepharose.

The best way to activate plasminogen into plasmin without contamination of the final preparation is to use an immobilized plasminogen activator. We have chosen urokinase over tPA or streptokinase because of several reasons. Urokinase, in contrast to streptokinase, cleaves plasminogen directly. Streptokinase is not an enzyme and its activation mechanism involves formation of a stoichiometric complex with plasminogen. Plasminogen activation by urokinase does not depend on the presence of fibrin as in the case of tPA. And urokinase is a human protein. These factors, and its relative inexpensiveness, make urokinase a preferable activator.

The ammonium sulfate precipitate of crude plasminogen was centrifuged at 14000 rpm and resuspended in a minimal volume using the 40 mM Tris, 10 mM Lys, 80 mM NaCl, pH 9.0 buffer to achieve the final concentration 10–15 mg/ml. Plasminogen solution was dialyzed overnight against the same buffer to get rid of ammonium sulfate. The dialyzed plasminogen solution (10–20 ml) was diluted with an equal volume of 100% glycerol and combined with 5 ml of urokinase-Sepharose which was prepared as described in the Material and Method section. The use of 50% glycerol is dictated by the need to avoid autodegradation of plasmin during activation. It was shown previously that plasmin is very stable in 50% glycerol and can be stored in this solution at $-20°$ C. for a long time. The activation occurred at room temperature for a period of time anywhere between 2 and 24 h depending on the freshness of urokinase-Sepahrose. With a new batch of urokinase-Sepharose, activation could be completed in 2 h. However, it deteriorates and becomes less efficient after several cycles, therefore, requiring the use of SDS-PAGE under reduced conditions to monitor the progress of plasminogen activation. Upon completion of activation, the plasmin solution was filtered from urokinase-Sepharose on a glass filter and immediately applied on benzamidine-Sepharose.

2. Capturing of Plasmin on Benzamidine-Sepharose.

The preferred way to purify proteins is affinity chromatography. Since the protein of interest is an active serine protease with trypsin-like specificity, benzamidine-Sepharose was chosen as an affinity sorbent which would allow the capture of only the active plasmin and would leave behind the various contaminants and plasminogen degradation products. We have purified ten batches of plasmin, each time refining the chromatographic conditions during first four preparations. The last six batches (which were used in studies described herein) were purified using the final chromatography protocol described below. Completely activated plasminogen solution in 50% glycerol was applied to the 50-ml benzamidine-Sepharose column equilibrated with 0.05 M Tris, pH 8.0, 0.5 M NaCl with a flow rate of 3 ml/min. The column was run at 3 ml/min at 4° C. As seen from the figure, the front portion of the non-bound peak contains high-molecular weight impurities typically present in crude plasminogen preparations. The rest of the non—bound peak is represented by residual non—activated plasminogen and by inactive autodegradation products of plasmin. NB1 peak does not have any plasmin or plasminogen activity whereas peak NB2 possesses a very small amount of residual plasminogen activity.

3. Elution of the Bound Plasmin with Low pH Buffer.

In order to preserve plasmin from inactivation at neutral pH, acidic elution conditions were chosen. The plasmin bound to benzamidine-Sepharose was eluted with 0.2 M glycine buffer, pH 3.0 containing 0.5 M NaCl. The bound peak was typically divided into three pools, small two front portions of the peak, B1 and B2, and the bulk of the eluted material, B3. As seen from the non-reduced gel, all these three pools contain highly pure (>95%) plasmin. However, the reduced gel, in addition to the heavy and light chains of plasmin, revealed some low molecular weight bands in a range of 10–15 kDa which resulted from partial degradation of the plasmin. Most likely, these bands represent internal cleavages in plasmin since they are visible only under the reduced conditions.

The front portion of the peak, B1, typically contains the most of the low molecular weight impurities. The B2 and B3 pools were less degraded, which was also evident as an increase in specific activity. The front portion of the bound peak had very little of the plasmin activity and was usually discarded. The loss of activity in this material can be explained by autodegradation during chromatography. This is because, first, there is no longer glycerol present in the eluted material and, second, the pH of the front portion is intermediate between the pH of the equilibrating and eluting buffers, typically in a range of pH 6–6.5. This led us to collect eluted plasmin into test tubes containing concentrated, 2 M glycine buffer, pH 3.0 (10% volume).

4. Formulation of Eluted Material in Acidified Water (pH 3.7).

Eluted plasmin was dialyzed with water which had been acidified to pH 3.7 with glacial acetic acid. Initially, this solvent condition was chosen simply to maintain active plasmin while preparing it for the future formulation procedures such as lyophilization, freezing, changing the solvent conditions and so on. All of these latter procedures are easier to perform with non-buffered, low-ionic strength solution. But we found that plasmin is extremely stable in acidified water and can be effectively used in this form for in vitro and in vivo studies.

The above described purification protocol has proved to be robust, reliable and reproducible. Benzamidine-Sepharose is capable of specific capture of the active plasmin, and this allows eliminating of the polishing gel-filtration step in Lys-plasminogen purification and might allow the use of crude plasminogen preparations as a starting material for plasmin production. Using this protocol, more than 500 mg of highly pure and active plasmin have been purified and submitted for pharmacology studies in the rabbit jugular vein thrombosis model.

On non-reduced and reduced SDS-PAGE, Bayer purified plasmin was compared with commercially available plasmin from Haematologic Technologies. In this gel, the purity of Bayer plasmin purified from Fraction II+III paste is comparable to that of commercial plasmin purified from whole plasma. Commercial plasmin had a slightly degraded heavy chain. Bayer plasmin, instead, has a small fraction of molecules with internal cleavages based on the low molecular bands seen on the reduced gel. Nevertheless, the most important fact is that their specific activities are also comparable, 21 and 24 CU/mg.

The gel also showed the degree of purification which can be achieved by affinity chromatography. In comparison with urokinase-Sepharose-activated plasminogen, plasmin purified by affinity chromatography lacks the high molecular impurities and non-activated plasminogen. As a result of affinity purification, the specific activity of plasmin is typically increased 1.5 times.

Another way to characterize plasmin is to test its inhibition by $\alpha_2$-antiplasmin. The mechanism of the inhibition involves plasmin cleavage of the reactive loop of $\alpha_2$-antiplasmin resulting in the formation of a covalent complex [Nilsson T. Wiman B. (1982) On the structure of the stable complex between plasmin and alpha-2-antiplasmin. *FEBS Lett*. 142(1):111–114]. Purified plasmin was mixed with the excess of purified $\alpha_2$-antiplasmin for 2 min and the samples were analyzed by non-reduced SDS-PAGE. The plasmin band almost completely disappeared and the new high molecular band, representing the plasmin-$\alpha_2$-antiplasmin complex, became visible. This is additional independent evidence which confirmed that plasmin purified in accordance with the above described protocol is fully active biologically.

It is known that plasminogen exists in two major forms, the native form with N-terminal glutamic acid, Glu-plasminogen, and the plasmin-cleaved form with lysine on the N-terminus, Lys-plasminogen. The species of plasmin being purified is not usually specified. In a separate experiment, we demonstrated that Glu-plasminogen activation into plasmin is accompanied by Glu- to Lys conversion and that the final plasmin is always Lys-plasmin (unless the activation is conducted in the presence of plasmin inhibitors, which was not the case in all our purifications). Therefore, for simplicity, as well as for avoiding confusion with Lys-plasminogen, we have preferred to drop the prefix Lys- in front of the word plasmin.

Stability of Plasmin

Being a typical serine protease, plasmin exhibits a bell-shaped pH dependence of its catalytic activity. As seen in FIG. 1, plasmin has maximum activity at pH 7.5–8.0, and its activity rapidly decreases at either more alkaline or more acidic pH's. Its known that plasmin is not active below pH 4.0, due to the protonation of histidine in the catalytic center [Robbins, K. C. and Summaria, L (1976) Plasminogen and Plasmin. *Meth. Enzymology*, 45:257–273; Castellino, F. J. and Powell, J. R. (1981) Human Plasminogen. *Meth. Enzymology*, 80: 365–378].

Plasmin formulated in acidified water (pH 3.7), is extremely stable. It can be kept in this form for months without any loss of activity or appearance of degradation products of proteolytic or acidic nature. FIG. 2 illustrates this by showing plasmin stability at 4° C. and at room temperature. At 4° C., plasmin is stable for at least nine months. Even at room temperature, plasmin does show very good stability at least for than two months. Long stability at room temperature is very important because it would make this formulation compatible with long regiments of thrombolytic administration. For example, 36 hr administration of thrombolytics is common in treatment of peripheral arterial occlusions.

The ability of acidified plasmin to become fully active upon transfer to physiological pH is evidenced by its activity in the caseinolytic assay and also in the $I^{125}$-fibrin-labeled clot lysis assays. Both of these assays are performed at pH 7.4, and we found complete recovery of plasmin activity during change of pH and passing through the iso-pI point (pH5–5.5). This is because plasmin is formulated in a non-buffered solvent and, when added to a buffered solution (either PBS of plasma), it adopts the neutral pH instantly and precipitation, which usually accompanies the slow passage through the iso-pI point, does not occur.

Thus, it appears to be that formulation of plasmin at low pH provides the basis for a reliable and stable theraputical composition. Such composition would allow administration of plasmin at room temperature without any fear that the drug might loss its potency during delivery or preparation. It would also be very convenient to avoid use of the ice-packed IV devices with jacketed and insulated lines which were used more than three decades ago when the first attempts to use active plasmin for thrombolysis were undertaken [Lippschutz, E. L., Ambrus, J. L., Ambrus, C. M., Constant, J., Rekate, A. C., Collins, G. L. and Sokal, J. E. (1965) Controlled study of the treatment of coronary occlusion with urokinase-activated human plasmin. Am.J.Cardiology, 16: 93–98; Ambrus, J. L., Ambrus, C. M., Sokal, J. E., Markus, G., Back, N., Stutzman, L., Razis, D., Ross, C. A., Smith, B. H., Rekate, A. C., Collins, G. L., Kline, D. L., and Fishman, J. B. (1960) Clinical Pharmacology of various types of fibrinolytic enzyme preparations. Am.J.Cardiology, 11: 462–475; Boyles, P. W., Meyer, W. H., Graff, J., Ashley, C. and Ripic, R. G. (1960) Comparative effectiveness of intravenous and intra-arterial fibrinolysin therapy. Am.J.Cardiology, 11: 439–446]. It is also important to note that, with acid-formulated plasmin, no evidence of activity loss during freezing-thawing or lyophilization has been noticed.

In Vitro Assessment

The first question we wanted to address is whether plasmin has the same intrinsic fibrinolytic potency as the plasminogen+plasminogen activator mixture. For this purpose, the fibrinolytic potency of plasmin was compared with that of a Lys-plasminogen+tPA mixture. These experiments were performed in a defined system consisting of radio-labeled fibrin clot which was submersed in PBS. FIG. 3 shows that, in a buffer environment, clot lysis achieved with plasmin is almost identical to the Lys-plasminogen+tPA mixture (curves a and b, respectively). At the same time, no clot lysis was observed with tPA alone (curve c) or in the absence of any proteins (curve d). These data indicate that, in the absence of inhibitors and other protein factors present in plasma, there is no difference in the ability to lyse fibrin clots between purified plasmin and Lys-plasminogen activated with tPA.

In order to assess thrombolytic potency of active plasmin, the $I^{125}$-fibrin-labeled clot lysis assay was performed with plasma clots in a plasma environment as described in the Materials and Method. The data in FIG. 4 demonstrate that plasmin is also efficacious in a plasma environment and is capable of dissolving plasma clots. This phenomenon is dose-dependent. At the same time, unlike with Lys-plasminogen+tPA, clot lysis by plasmin does not progress to completion in a plasma environment; clot lysis tends to level off after 2 hr. This phenomenon could be explained by the presence of various protease inhibitors in a plasma environment and, especially, by quick inhibition of non-clot-bound plasmin by $\alpha_2$-antiplasmin.

In order to assess the role of plasma inhibitors in plasmin-catalyzed clot lysis, a series of clot lysis experiments was performed with samples lacking $\alpha_2$-antiplasmin, $\alpha_2$-macroglobulin or all the inhibitors. The results of this study are summarized in FIG. 5. As seen in this figure, clot lysis was enhanced by deletion of either $\alpha_2$-antiplasmin or $\alpha_2$-macroglobulin in plasma surrounding the clot, as well as by the deletion of all inhibitors (i.e. in PBS). These results indicate that clot lysis by plasmin is under very strict control by the endogenous inhibitors. It appears that, in contrast to plasminogen activator—induced thrombolysis, clot lysis with plasmin can be very well controlled by these inhibitors. Plasminogen activator—induced thrombolysis utilizes the internal source of plasminogen present in plasma which, from the practical point of view, is unlimited in a human body. On the other hand, plasmin-induced thrombolysis entirely depends on the external source of the plasmin. Therefore, cessation of plasmin administration should result in rapid cessation of thrombolysis and should provide a basis for safer thrombolytic therapy.

In Vivo Results (a) Radiolabeled Clot (% lysis)

The % lysis of radiolabeled clots and consumption of factor VIII and fibrinogen are shown at 60 minutes (FIG. 6) and 90 minutes (FIG. 7). At 0.5 mg/kg and 1.0 mg/kg, tPA induced 16±2% and 21±2% lysis, respectively, whereas plasmin at 1.0 mg/kg and 2.0 mg/kg induced 26±3% and 33±4% lysis, respectively. At 90 minutes, tPA infusion had resulted in 21±2% and 26±2% lysis, respectively, compared to plasmin which induced lysis of 31±4% and 36±2%, respectively.

(b) Restoration of Venous Flow (Flow probe)

The % restoration of venous blood flow and consumption of factor VIII and fibrinogen are shown at 60 minutes in FIG. 8 and and at 90 minutes in FIG. 9. At doses of 0.5 mg/kg and 1.0 mg/kg tPA induced 16±4% and 21±10% restoration of baseline blood flow at 60 minutes, respectively, whereas plasmin at 1.0 mg/kg and 2.0 mg/kg induced 20±1% and 33±% restoration of baseline blood flow, respectively. At 90 minutes, tPA infusion had resulted in 18±3% and 26±11% restoration of blood flow, respectively and plasmin had resulted in 25±5% and 34±6% restoration of flow, respectively.

(c) Cuticle Bleeding Times

Cuticle Bleeding times at 60 minutes are shown in FIG. 10. Saline treatment resulted in bleeding times of 13±1 minutes. t-PA at doses of 0.5 mg/kg and 1.0 mg/kg resulted in bleeding times of 13±2 and 25±4 minutes, respectively, whereas plasmin, at doses of 1.0 mg/kg and 2.0 mg/kg resulted in bleeding times of 17±3 and 19±1 minutes, respectively.

(d) Risk/Benefit Assessment of Plasmin Treatment

We completed an extensive comparative pharmacological evaluation (risk/benefit) of plasmin in the rabbit model of thrombolysis. The efficacy of plasmin was compared with that of tPA. We utilized % lysis and restoration of blood flow as indices of efficacy. These analysis were performed in separate experiments. Concomitantly, we compared respective side effects induced by these thrombolytic agents by measuring the consumption of Factor VIII and Fibrinogen and assessing bleeding times. This allowed us to determine an approximate benefit/risk profile. To determine the risk profile, we calculated the ED50 dose for tPA, using the consumption of Factor VIII as a surrogate marker for induction of the lytic state and bleeding. We verified that the consumption of Factor VIII was directly related to the bleeding side effect by replenishing back Factor VIII (Kogenate®) and returning normal hemostasis. We examined tPA doses ranging from 0.1 mg/kg to 3.0 mg/kg with a N of at least 10 animals/dose. For comparison, 1.0 mg/kg is the clinical dose for tPA. The calculated ED50 for tPA was 1.8 mg/kg. We performed a similar calculation for locally administered plasmin and calculated an ED50 of 3.6 mg/kg (See FIG. 11 Since the molecular weights of plasmin and tPA are similar, we concluded that twice the dose of plasmin (wt basis) induced similar bleeding side effects as tPA. We then evaluated efficacy (% lysis and blood flow) with doses of tPA and plasmin with equivalent risk profiles i.e., consumption of coagulation proteins and bleeding (FIG. 12). At all equivalent risk doses tested, tPA (0.5–3.0 mg/kg) and plasmin (1.0–3.0 mg/kg), plasmin induced similar (if not significantly better) rates of lysis and restoration of blood flow compared to tPA. Thus, we conclude that the pharmacological data presented in this report is sufficient to recommend that plasmin be considered for DP0 for the lytic treatment of thrombi accessible by catheter placement.

The above examples are intended to illustrate the invention and it is thought variations will occur to those skilled in the art. Accordingly, it is intended that the scope of the invention should be limited only by the claims below.

What is claimed is:

1. A method of thrombolysis comprising, admininstering active plasmin directly to a clot, wherein the active plasmin is at least about 95% pure, and wherein the active plasmin is a stable liquid formulation at a pH of less than about 4.

2. The method of claim 1, wherein administering the active plasmin is accomplished by direct catheter delivery.

3. The method of claim 1 wherein the clot is in a distal human limb.

4. The method of claim 1 wherein the clot is in a catheter.

5. The method of claim 1, wherein the active plasmin is free of plasminogen activator.

* * * * *